United States Patent [19]

Cunningham

[11] Patent Number: 4,577,502
[45] Date of Patent: Mar. 25, 1986

[54] CONVEYOR BELT MONITOR

[75] Inventor: Jock B. Cunningham, Mount Isa, Australia

[73] Assignee: Mount Isa Mines Limited, Queensland, Australia

[21] Appl. No.: 620,015

[22] Filed: Jun. 13, 1984

Related U.S. Application Data

[63] Continuation-in-part of Ser. No. 390,665, Jun. 21, 1982, abandoned.

[30] Foreign Application Priority Data

Jun. 29, 1981 [AU] Australia .............................. PE9491

[51] Int. Cl.$^4$ ............................................ G01N 29/04
[52] U.S. Cl. ....................................... 73/600; 73/159; 73/644; 340/676
[58] Field of Search ................. 73/159, 599, 600, 644; 340/675, 676

[56] References Cited

U.S. PATENT DOCUMENTS

| | | |
|---|---|---|
| 3,190,111 | 6/1965 | Trussell et al. ....................... 73/600 |
| 3,289,468 | 12/1966 | Van Der Veer et al. ............ 73/644 |
| 4,253,337 | 3/1981 | Vasile ..................................... 73/600 |
| 4,291,577 | 9/1981 | Baum et al. ........................... 73/159 |
| 4,519,249 | 5/1985 | Hunt ...................................... 73/159 |

Primary Examiner—Stewart J. Levy
Assistant Examiner—John E. Chapman, Jr.
Attorney, Agent, or Firm—Darby & Darby

[57] ABSTRACT

Flaws may be detected in conveyor belting in motion by transmitting ultrasound to the belting at one zone, detecting ultrasound propagated by the belting from the one zone to another zone spaced apart from the first and issuing a signal responsive to any ultrasound detected, whereby a signal is obtained which is indicative of discontinuities in the belting intermediate the zones. Preferably, a column of water extending between an ultrasonic transducer and the belt is used for ultrasonic coupling during motion of the belt, and tracking means are provided to maintain the column at constant length. With proper frequency selection, ultrasound can be transmitted a surprising distance through conveyor belting made of rubber-like material.

25 Claims, 7 Drawing Figures

CONVEYOR BELT MONITOR

This is a continuation-in-part of application Ser. No. 390,665, filed June 21, 1982, now abandoned.

This invention relates to a method and apparatus for detecting a rip or flaw in a conveyor belt.

Conveyor belts comprising rubber or rubberlike materials are in some uses susceptible to failure by tearing or ripping. Early detection of flaws that may lead to such failure is desirable to prevent loss of conveyed materials and possible damage to associated equipment and injury to attending personnel.

For that purpose various means such as trip cords and tilt trays have been used mechanically to detect material falling through a tear in the conveyor belt. Such monitors are only sensitive to a gaping rip sufficient to permit material to fall through, or to gross belt failure.

In another method the electrical continuity of electrical conductors embedded in the belt composition is monitored. However, that method requires the use of expensive and non-standard belts, and it is difficult to maintain the conductors in a production environment.

Of the methods employed to date, all are either insensitive to some ways in which a belt can rip or are otherwise impractical.

It would be particularly advantageous if a flaw or incipient flaw likely to result in belt failure could be detected so that preventive maintenance could be conducted. None of the methods hitherto proposed for monitoring conveyor belts has been useful for that purpose.

SUMMARY OF THE INVENTION

The present invention uses ultrasonic vibrations, referred to hereinafter as "ultrasound", for the purpose of detecting discontinuities in the belting.

It has hitherto been believed that transmission of ultrasound in rubber over distances of more than a few centimeters was impracticable because of the high level of attenuation of ultrasound in rubber. It was also thought that attenuation would decrease continuously with decreasing frequency.

The present invention stems from the discovery that ultrasound may be propagated in belting comprising a rubber or rubberlike composition, and that particular frequencies of ultrasound are attenuated to a much lesser degree than expected and to a lesser degree than other, higher or lower, frequencies.

The particular frequencies may be ascertained by experiment for a particular belting composition and belting thickness. There may be more than one particular frequency at which the attenuation is low in comparison with neighboring frequencies.

Surprisingly, it has been found possible to select an ultrasound frequency at which attenuation in belting is sufficiently low that a transmitter and receiver may be spaced part over a long path length, for example a meter or more, enabling a transmitter and receiver to be situated adjacent opposite side edges of an industrial scale conveyor belt. Moreover, the low attenuation enables a reliable signal to be propagated and detected at a distance from the transmitter even when the intervening conveyor belting is of a poor quality but intact.

Preferred embodiments of the method of the invention also permit small discontinuities throughout the length of a belt to be discovered while the belt is in normal use and enable identification of portions requiring preventive maintenance to reduce the risk of a rip subsequently occurring.

According to a first aspect, the invention consists in a method for testing a conveyor belting comprising the steps of:

transmitting ultrasound to the belting at a first zone;
detecting ultrasound propagated by the belting from the first zone to a second zone spaced apart from the first; and
issuing a signal responsive to ultrasound, if any, so detected, whereby said signal is indicative of discontinuities in the belting intermediate said zones.

According to a second aspect the invention consists in apparatus comprising:

a conveyor belt passing through a first zone and a second zone spaced from the first;
transducer means for producing ultrasound;
coupling means for transmitting the ultrasound to the belt while it is in motion through the first zone; and
sensor means producing a signal responsive to ultrasound vibrations in the belt at the second zone.

In preferred embodiments the invention is used to monitor a conveyor belt while in motion. Ultrasound generated by a piezoelectric transducer is transmitted to a moving belt via a liquid or aqueous medium impinging on the underside of the belting at a first zone. The ultrasound is propagated along the belting to a second zone at which a detector produces a signal responsive to ultrasound, also coupled to it via a liquid or aqueous medium. Variations in the received signal are indicative of discontinuities or flaws of the belting intermediate the zones. Preferably, the zones are spaced apart on a line perpendicular to the direction of travel of the belt.

BRIEF DESCRIPTION OF THE DRAWINGS

By way of example only an embodiment of apparatus according to the invention will now be described with reference to the accompanying drawings, wherein.

DESCRIPTION OF THE PREFERRED EMBODIMENTS

Figure 1:
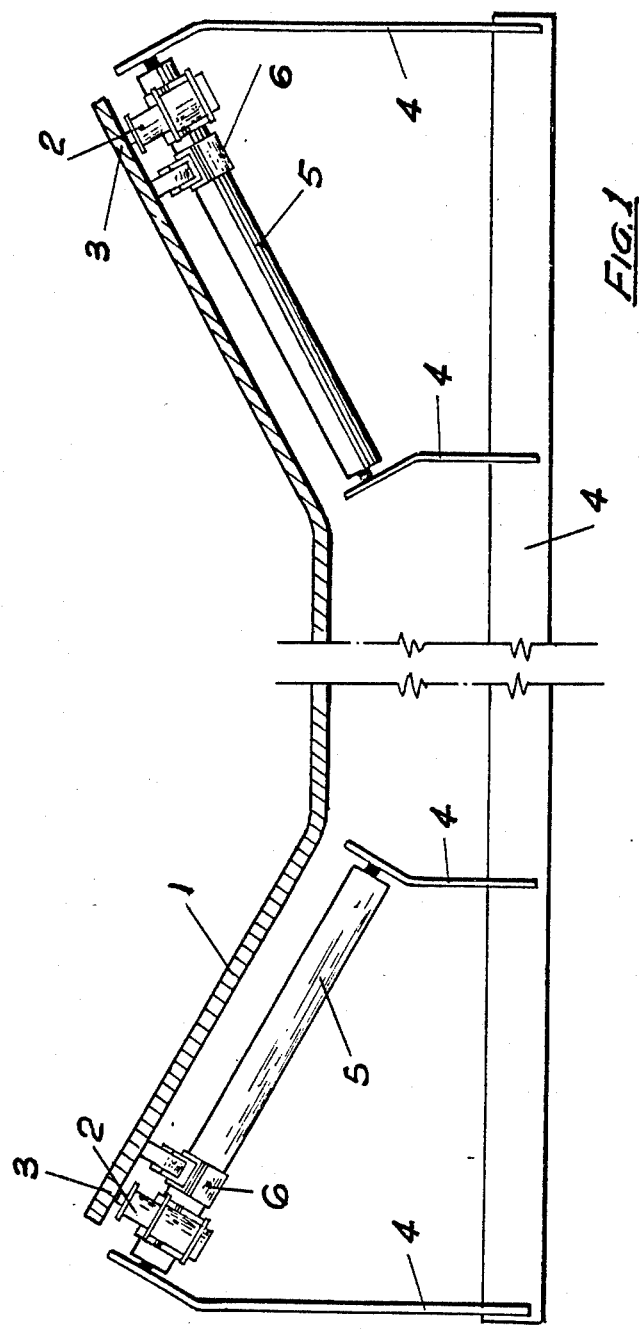
FIG. 1 is a cross section through an endless conveyor belt, transverse the direction of conveyor travel, showing a general arrangement according to the invention.

FIG. 1 shows a cross section through an endless conveyor belt 1, transverse the direction of conveyor travel.

The conveyor has a trough-shaped cross section, and belting 1 is supported along its length by means not shown in FIG. 1.

The conveyor belting 1 is typical of the kind used in the mining industry comprising a steel-cord-reinforced rubberlike composition having a width edge-to-edge of 1–2 meters and having a thickness in the present example of 20 or 25 mm.

A first transducer assembly 2 is mounted adjacent to and beneath conveyor belt 1 near one edge of the conveyor and a second transducer assembly 2 is similarly mounted near the opposite edge. One transducer assembly 2 together with associated circuitry is a means for producing ultrasound and the other with associated circuitry acts as a detector of ultrasound.

In use a column of water extends between each transducer assembly 2 and a zone 3 of belt 1 overlying that transducer assembly.

Ultrasound may thus be transmitted from one transducer assembly 2 via a water column extending from the transducer to a zone 3 of belt 1, through belt 1 to a second zone 3 over lying the other transducer assembly, and via a water column to ultrasound detection means associated with the other transducer assembly 2.

A discontinuity in belt 1 between zones 3 may thus be detected.

Figure 2:
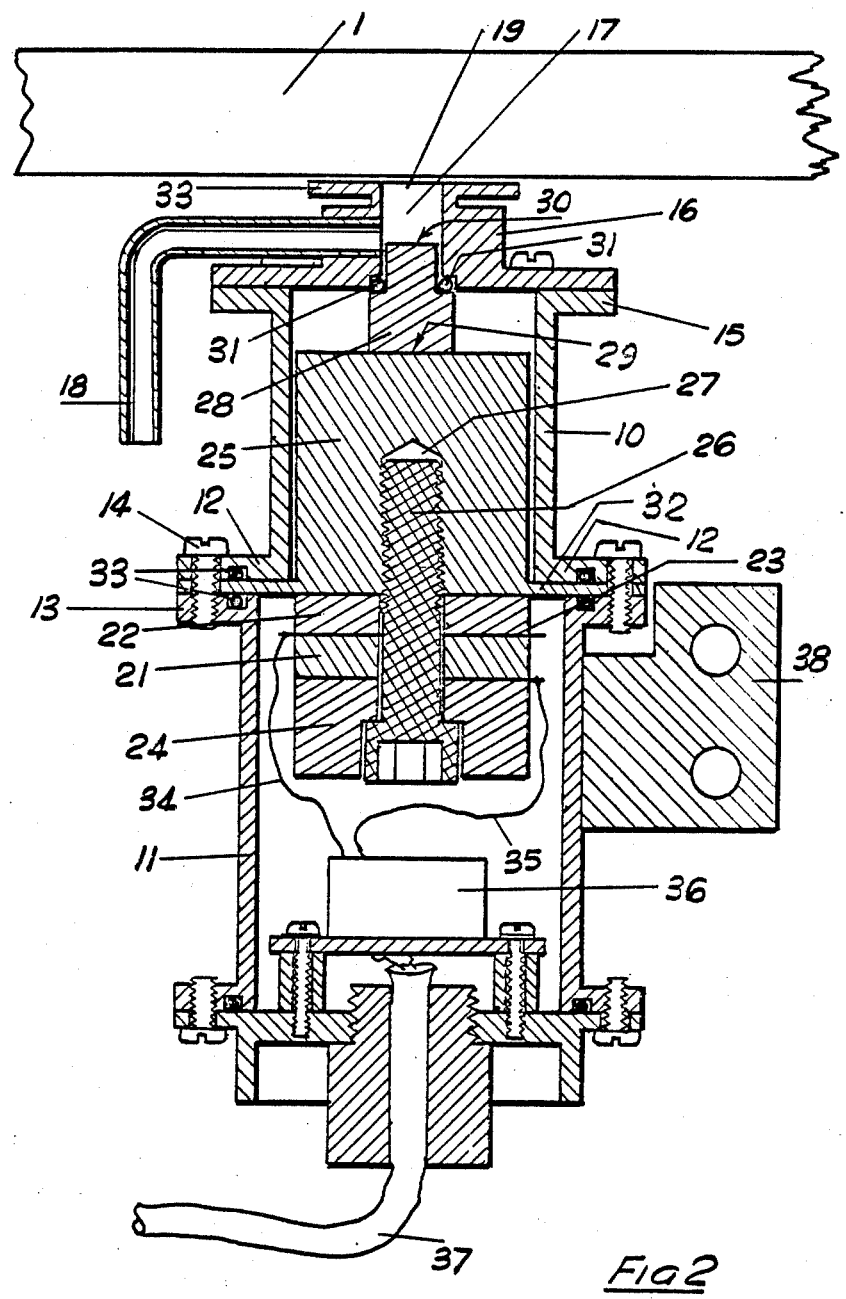
FIG. 2 is a cross section of a transducer assembly employed in accordance with the invention for transmitting ultrasound to a conveyor belt in motion.

FIG. 2 shows in cross section a transducer assembly 2 useful either for transmitting ultrasound to a belt 1 in motion or for detecting ultrasound in the belt 1. The transducer assembly 2 comprises an upper tubular case part 10 and a lower tubular case part 11 connected at respective radially extending flanges 12 and 13 by fasteners 14.

Upper case part 10 has an upper radially extending flange 15 to which is mounted a head or case 16 defining a chamber or cavity 17 provided with a water inlet tube 18 and a water outlet orifice 19.

Case parts 10 and 11 house a subassembly comprising two discs 21, 22 of piezoelectric material (such as Philips PXE 42) separated at adjacent faces by metallic foil 23. The discs 21, 22 and foil 23 are sleeve-mounted on a bolt 26 and clamped coaxially between metal cylinders 24 and 25 by the bolt 26, which extends through the cylinder 24, the discs 21 and 22, and the foil 23 and threadably engages a threaded blind bore 27 formed in the cylinder 25.

A cylindrical plug 28 of a nonmetallic solid material, typically a plastics substance, is fixed at one end 29 to the upper face of the metal cylinder 25. The other end 30 of the plug 28 is of reduced diameter over a length extending into the cavity 17. An O-ring 31 provides a seal between the plug 28 and the case 16.

The cylinder 25 is provided with a radially extending flange 32 which is clamped between O-rings 33 grooved in case flanges 12 and 13, whereby the piezoelectric crystal subassembly is mounted.

An electrical connection 34 with the metallic foil 23 serves as a connection to one electric pole of piezoelectric discs 21, 22.

The other electrical pole is kept at ground potential by a connection 35 of the end face of the disc 21 remote from the foil 23 to ground potential and by connection of the end face of the disc 22 remote from the foil 23 to the cylinder 25, which is grounded. The cylinders 24 and 25 are of dissimilar metal, and the axial lengths are chosen having regard to the velocity of ultrasound in the respective metals. The combined subassembly connected by bolt 26 can vibrate substantially in the axial direction at ultrasonic frequencies with a fundamental resonance frequency occurring when the wavelength of the vibration is equal to twice the combined axial dimension.

When the apparatus is used as a transmitter, water fed under pressure via the inlet tube 18 to the cavity 17 flows outwardly from the orifice 19 and impinges on the underside of the overlying conveyor belt 1.

A continuous column of water thus extends between the ultrasound transmitting face 30 of the plug 28 and the overlying zone of the belt 1, providing an ultrasound coupling medium, notwithstanding motion of the belt. A flange 33 surrounding the orifice 19 assists in maintaining the water column while the conveyor belt 1 is in motion.

The ultrasonic receiver and transmitter are similar in design and differ in respect of an electric circuit 36 shown schematically. This circuit is of a type well known in the art and comprises an impedance-matching inductor in the transmitter and in the receiver a similar inductor in addition to a preamplifier. In the case of the transmitter, electrical signals supplied through a cable 37 are converted to ultrasonic vibrations according to the piezoelectric effect, and in the receiver the vibrations are converted to electric signals by the piezoelectric effect and amplified by the preamplifier for subsequent analysis. A lug 38 is fixed to the case 11 to facilitate mounting.

Figure 3:
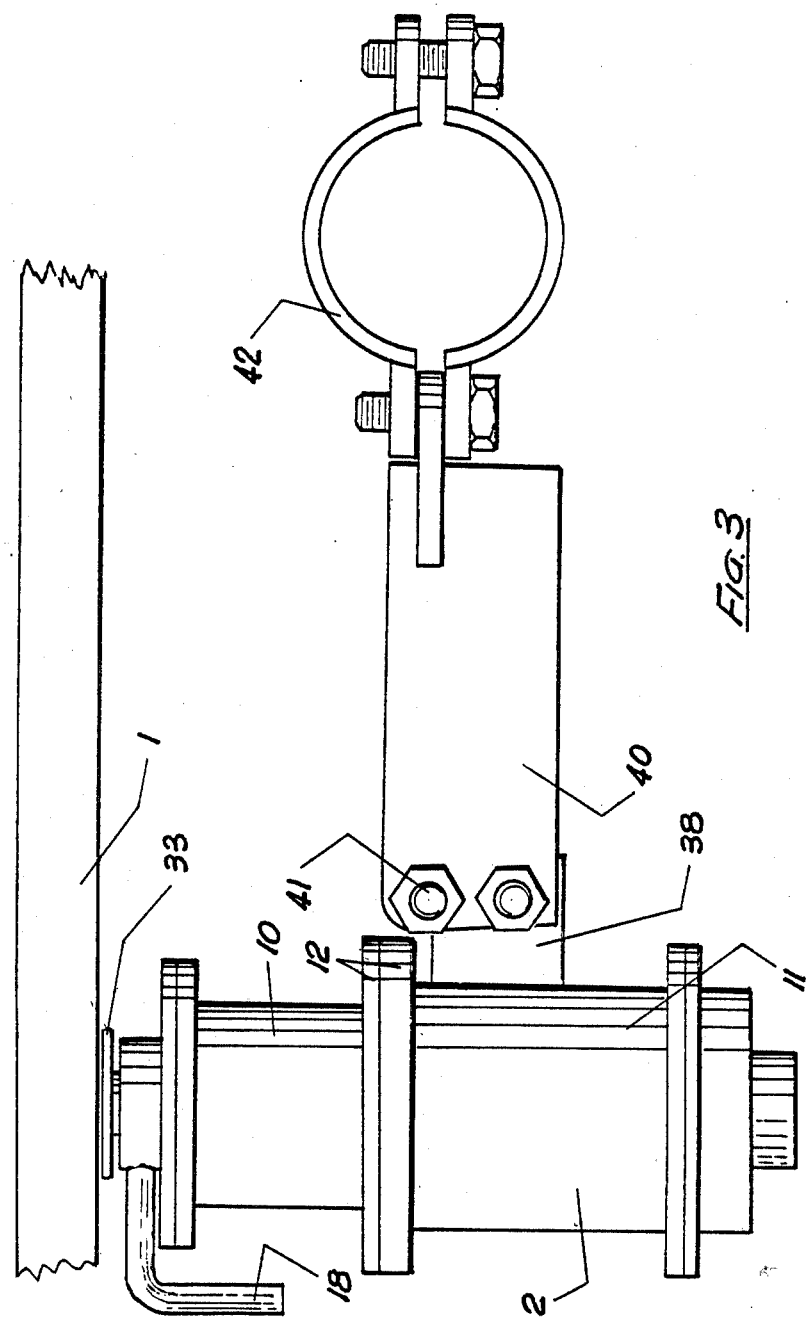
FIG. 3 shows one part of the means for mounting the apparatus of FIG. 2 in the arrangement of FIG. 1.

FIG. 3 shows a means of mounting the transducer assembly 2 (referring collectively to the receiver and transmitter) relative to the conveyor belt 1. The transducer assembly 2 is fixed to a lever arm 40 by bolts 41 through the lug 38 in a way that allows a small rotation about axes through the bolts 41 so as to adjust and fix the angle of the axis of the transducer with respect to the surfaces of the belt 1. The lever arm 40 is fixed to a pipe clamp 42 by a lug 43. The pipe clamp 42 attaches over a roller 5 shown in FIGS. 1 and 4. The roller 5 is modified from a typical idler roller and forms a pivot axis for the transducer assembly 2 so that the transducer assembly 2 can follow the random vertical movements of the belt 1.

Figure 4:
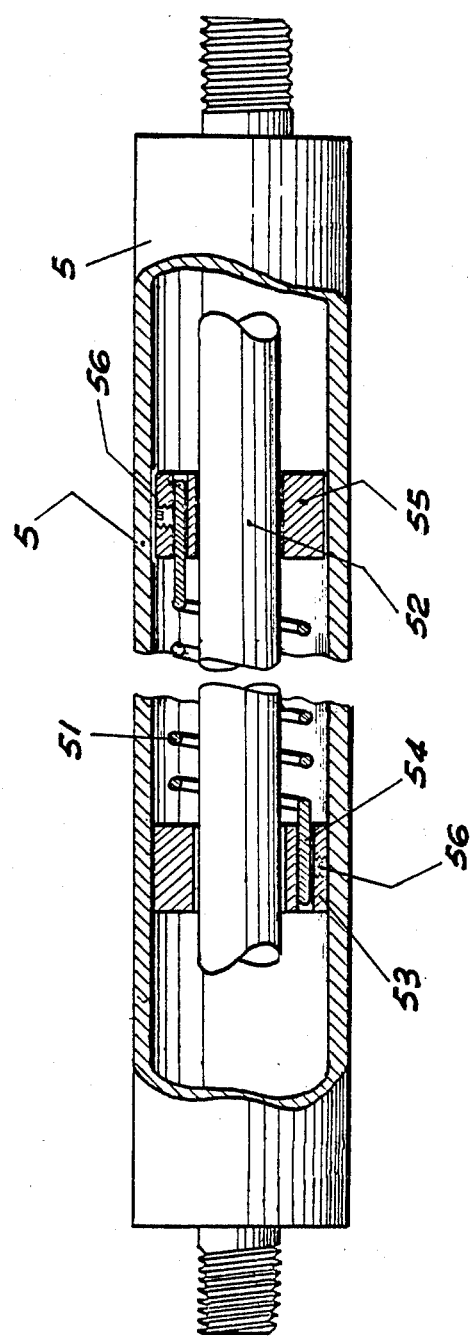
FIG. 4 shows a second part of the means for mounting the apparatus of FIG. 2 in the arrangement of FIG. 1.

As FIG. 4 shows, roller 5 is provided with a helical spring 51 mounted coaxially in the roller, whereby a restoring torque acts on the roller with respect to the fixed shaft 52 and in turn exerts an upward force on the transducer 2 relative to the conveyor belts 1. The spring 51 is secured at one end 54 to the roller 5 by a collet 53 which is fastened by a screw 56 to the inside wall of the roller 5 and is free of the shaft 52.

The other end 54' of the spring 51 is secured to the shaft 52 by a similar collet 55 which is free of the inside wall of the roller 5. Each end of the spring 51 is fastened to the respective collet 53 or 55 by a grub screw 56 (not sectioned).

Figure 5:
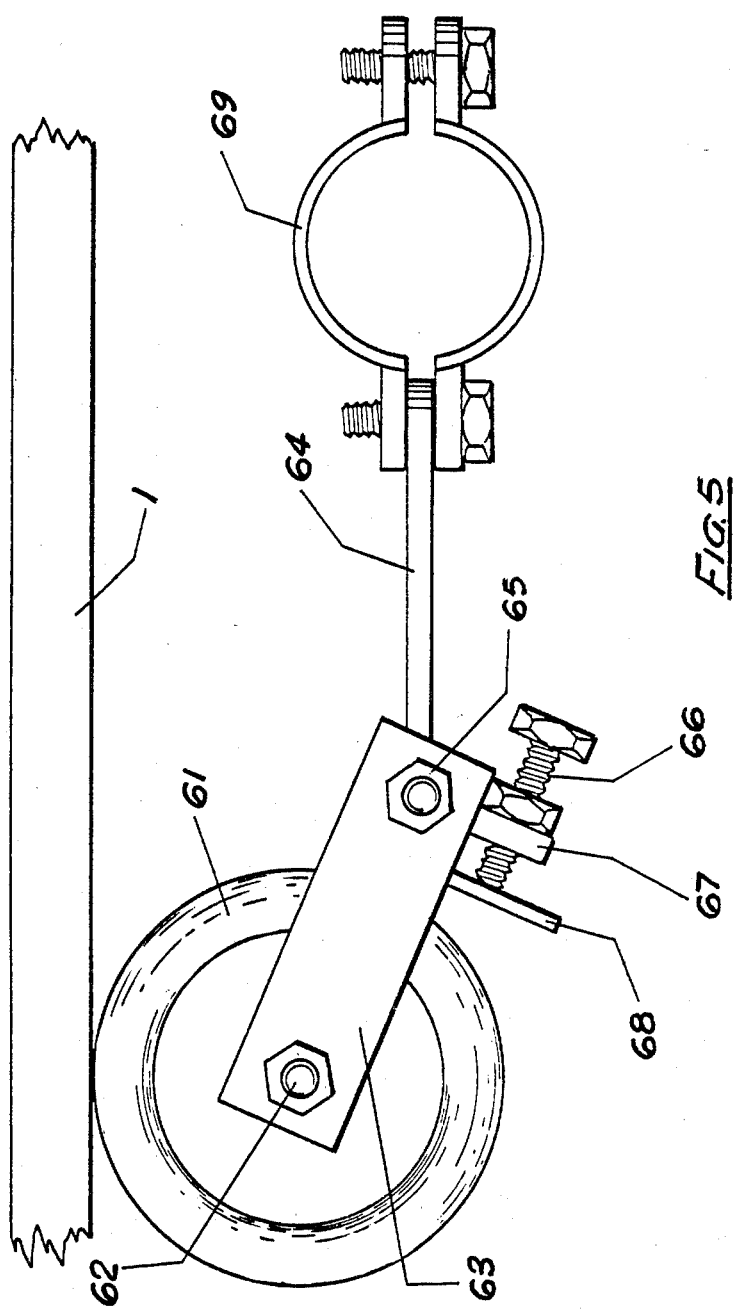
FIG. 5 shows a third part of the means for mounting the apparatus of FIG. 2 in the arrangement of FIG. 1.

Attached to the same roller 5 is a wheel arrangement 6 shown in FIG. 5. The separation of the face of the transducer 2 at the orifice 19 (FIG. 2) from the surface of the belt 1 is is controlled by the wheel arrangement 6. A wheel 61 is mounted on an axle 62 supported by a fork 63 which is in turn mounted on a lever arm 64 at pivot axle 65. This arrangement allows for the rotation of the wheel 61 about the axis of axle 65 so as to effectively adjust the separation of the axle 65 from the belt 1. Adjustment is made by a screw 66 which is screwed into a lug 67 attached rigidly to the lever arm 64 and acts on a lug 68 which is rigidly attached to the fork 63. The assembly is clamped adjacent to the transducer 2 on the roller 5 by a clamp 69 similar to the clamp 42. Adjustment of the screw 66 results in rotation of the roller 5 and a change in the separation of the transducer 2 from the belt 1. Contact of the wheel 61 and the belt 1 is maintained by the roller spring 51.

As FIG. 1 shows, rollers 5 are mounted in the usual way on an idler frame 4. The transmitter transducer assembly 2 with an associated wheel 6 is mounted so as to transmit ultrasound into one edge of the belt 1, and the receiver transducer assembly 2 with its associated wheel 6 is mounted on the opposite roller 5 to detect ultrasound at the other edge of the belt 1.

Electrical energy is supplied to the transmitter at a frequency preferably equal to the fundamental resonant frequency of that transmitter in a series of short pulses. Also preferably the frequency is such that the wavelength of ultrasound in the conveyor belt is equal to the thickness of the belt 1.

When the ultrasound is of a particular frequency such that the wavelength in the belting 1 is equal or similar in dimension to the belting thickness dimension, the ultrasound attenuation is of the order of only 0.5–0.65 dB per cm of path length, whereas at neighboring higher and lower frequencies the attenuation is significantly greater.

Figure 7:
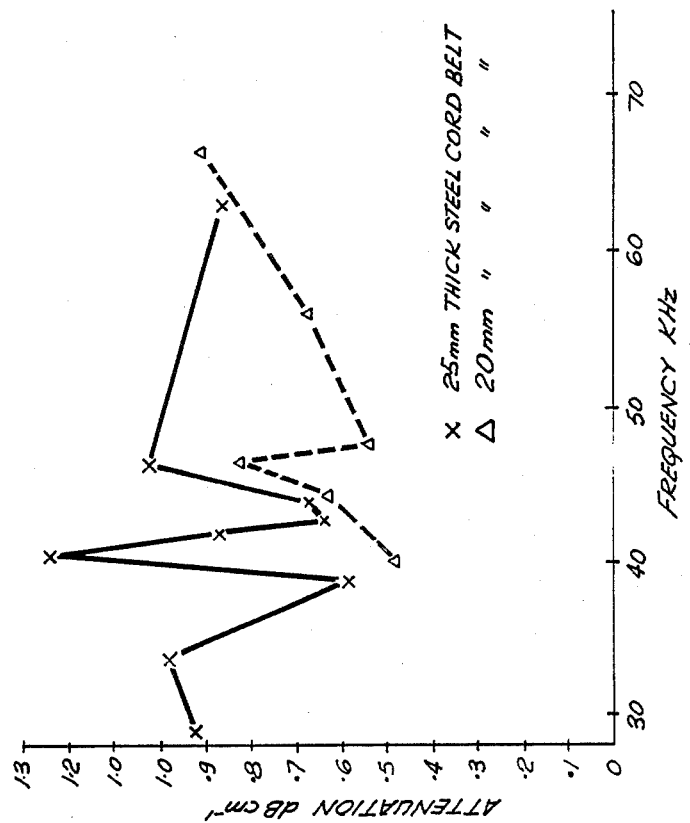
FIG. 7 is a graph showing frequency dependence of ultrasound attenuation in conveyor belting which is subjected to testing in accordance with the invention.

FIG. 7 shows a plot of ultrasound attenuation in decibels per centimeter of path length against frequency in beltings of different thicknesses. In a steel-cord-reinforced belting of 25 mm thickness and at frequency of 43.5 kHz, the wavelength is about 25 mm and the attenuation is at or near a minimum. By selecting a frequency of 43.5 kHz, ultrasound can be propagated and detected over a path length exceeding one meter in the 25 mm thick belt. At a frequency of 30 kHz the signal strength at 1 meter is about 35 times lower than at 43.5 kHz and would be difficult if not impossible to detect reliably by practicle means. Likewise for a belt of similar construction but of thickness 20 mm, at a frequency of 47.6 kHz the ultrasound wavelength is about 21 mm and attenuation is at or near a minimum.

As is apparent from FIG. 7, there is another attenuation minimum for the 25 mm thickness belting at around 39 kHz.

As will be apparent to those skilled in the art, the frequency is desirably selected having regard both to the level of attenuation and the sensitivity of attenuation to slight change in frequency.

Signals from the receiver are amplified, rectified and sampled at a certain time following each pulse of electrical energy supplied to the transmitter. This delay takes into account the time that the resultant pulse of ultrasound takes to travel from the transmitter to the receiver. An alarm circuit monitors the level of ultrasound and issues an alarm if this level falls below an adjustable threshold for an adjustable period of time. This alarm is also inhibited if certain functions of the apparatus are not operational. Such functions include power supplies and coupling water supply. Thus, the apparatus can be adjusted to be responsive to rips and other faults that are of a predetermined severity and/or of a certain minimum length. The conveyor belt drive motor is stopped if all alarm conditions apply.

Figure 6:
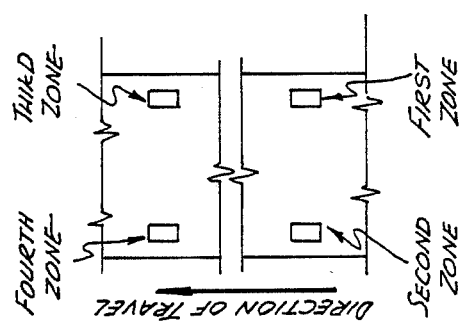
FIG. 6 is a fragmentary diagrammatic plan view showing the relative positions of four zones in accordance with the invention with respect to a belt undergoing test.

The apparatus described is normally mounted at a location on the conveyor belt 1 so that it monitors the belt 1 immediately after passing through areas where rips are likely to occur. These locations are usually immediately downstream of the point where the belt 1 is loaded. One problem occurs when the conveyor belt 1 contains relatively long sections that, because of their poor physical condition, do not satisfactorily transmit ultrasound. The belt rip detector can be made insensitive to these sections by increasing the response time of the alarm circuit. This, however, also increases the minimum length of rip capable of being detected. To overcome this problem a second rip detector is mounted to monitor the belt immediately before passing through the area where a rip is most likely to occur. Thus, the first rip detector comprises a pair of transducers respectively mounted in first and second zones, and the second rip detector comprises a pair of transducers respectively mounted in third and fourth zones, as shown in FIG. 6. The third and fourth zones are respectively spaced apart from the first and second zones in a direction parallel to the direction of belt travel. The conveyor belt drive motor is stopped only if the condition of the belt has deteriorated between the two rip detectors.

Another application of the apparatus relates to its use for detecting long term degradation of the belt and identifying sections that require preventive maintenance. This is done by compiling a log of the level of received ultrasound throughout the entire length of the belt. In addition, as an alternative condition for raising an alarm, the log is compared in real time with the actual received level of ultrasound and an alarm is raised when the actual level differs from the log.

Thus, there is provided in accordance with the invention a novel and highly-effective method and apparatus for detecting a rip or flaw in a conveyor belt. Many modifications of the preferred embodiments of the invention disclosed herein can readily by made by those skilled in the art without departing from the spirit and scope of the invention. Accordingly, the invention is not limited except by the appended claims.

What is claimed is:

1. A method for testing a conveyor belt comprising the steps of:
   (a) transmitting ultrasound to the belt at a first zone;
   (b) detecting ultrasound propagated by the belt from the first zone to a second zone spaced apart from the first; and
   (c) issuing a signal responsive to ultrasound, if any, so detected, whereby said signal is indicative of discontinuities in the belt intermediate said zones;
   wherein the first and second zones are spaced apart in a direction transverse the direction of belt travel, further comprising the steps of:
   (a) transmitting further ultrasound to the belt at a third zone spaced apart from the first in the direction of travel of the belt;
   (b) detecting any said further ultrasound propagated by the belt from the third zone at a fourth zone spaced apart from the third in a direction transverse the direction of travel of the belt;
   (c) issuing a second signal responsive to said further ultrasound, if any, so detected, whereby to indicate a discontinuity between the third and fourth zones, and
   (d) correlating the second signal with the first.

2. A method according to claim 1 further including the step of coupling the transducer with a belt in motion via a column of water extending between the transducer and the belt.

3. A method according to claim 2 further comprising the step of tracking vertical movement of the belt and moving the transducer upwardly or downwardly so as to maintain a substantially constant length of water column between the transducer and the belt.

4. A method according to claim 3 wherein the particular frequency is selected by measuring the change in attenuation of ultrasound in the belt with change in ultrasound frequency so that attenuation is at or near a minimum.

5. A method according to claim 4 wherein said ultrasound is transmitted to the belt while the belt is in motion through the zones.

6. A method according to claim 4 wherein the first and second zones are at or adjacent to opposite side edges of the conveyor belt.

7. A method for detecting a rip in a conveyor belt comprising a rubber or rubberlike composition, the method comprising the steps of:
(a) transmitting ultrasound of a particular frequency to the belt at a first zone;
(b) detecting ultrasound of said particular frequency propagated by the belt from the first zone to a second zone spaced apart from the first; and
(c) issuing a signal responsive to the intensity of ultrasound, if any, so detected, whereby said signal is indicative of discontinuities in the belt intermediate said zones.

8. A method according to claim 7 wherein said ultrasound is transmitted to the belt while the belting is in motion through the zones.

9. A method according to claim 8 wherein the first and second zones are spaced apart in a direction transverse the direction of belt travel, further comprising the steps of
(a) transmitting further ultrasound to the belt at a third zone spaced apart from the first in the direction of travel of the belt;
(b) detecting any said further ultrasound propagated by the belt from the third zone at a fourth zone spaced apart from the third in a direction transverse the direction of travel of the belt;
(c) issuing a second signal responsive to said further ultrasound, if any, so detected, whereby to indicate a discontinuity between the third and fourth zones; and
(d) correlating the second signal with the first.

10. A method according to claim 8 further including the step of coupling the transducer with a belt in motion via a column of water extending between the transducer and the belt.

11. A method according to claim 10 further comprising the step of tracking vertical movement of the belt and moving the transducer upwardly or downwardly so as to maintain a substantially constant length of water column between the transducer and the belt.

12. A method according to claim 7 wherein the first zone and second zone are at or adjacent to opposite side edges of the conveyor belt.

13. A method according to claim 7 wherein the particular frequency is selected so that the wavelength of the ultrasound in the belt is of a dimension equal to or similar to the thickness dimension of the belt.

14. A method according to claim 13 wherein said ultrasound is transmitted to the belt while the belt is in motion through the zones.

15. A method according to claim 14 wherein the first and second zones are spaced apart in a direction transverse the direction of belt travel, further comprising the steps of:
(a) transmitting further ultrasound to the belt at a third zone spaced apart from the first in the direction of travel of the belt;
(b) detecting any said further ultrasound propagated by the belt from the third zone at a fourth zone spaced apart from the third in a direction transverse the direction of travel of the belt;
(c) issuing a second signal responsive to said further ultrasound, if any, so detected, whereby to indicate a discontinuity between the third and fourth zones; and
(d) correlating the second signal with the first.

16. A method according to claim 14 further including the step of coupling the transducer with a belt in motion via a column of water extending between the transducer and the belt.

17. A method according to claim 16 further comprising the step of tracking vertical movement of the belt and moving the transducer upwardly or downwardly so as to maintain a substantially constant length of water column between the transducer and the belt.

18. A method according to claim 13 wherein the first and second zones are at or adjacent to opposite side edges of the conveyor belt.

19. Apparatus comprising,
a conveyor belt comprising a rubber or rubberlike material, the belt passing through a first zone and a second zone spaced from the first;
transducer means for producing ultrasound at a predetermined frequency;
coupling means for transmitting said ultrasound to the belt while it is in motion through the the first zone; and
sensor means producing a signal responsive to the intensity of said ultrasound, if any, in the belt at the second zone, whereby said signal is indicative of discontinuities in the belt.

20. Apparatus according to claim 19 wherein the ultrasound is of a frequency selected so that the attenuation of ultrasound in the belt is at or near a minimum.

21. Apparatus according to claim 19 wherein the ultrasound is of a frequency selected so that the wavelength of the ultrasound in the belt is of a dimension equal to or similar to the thickness dimension of the belt.

22. Apparatus according to claim 19 wherein the first zone and the second zone are at or adjacent opposite side edges of the belt.

23. Apparatus according to claim 19 wherein the coupling means includes a liquid medium.

24. Apparatus according to claim 19 further comprising tracking means for maintaining a substantially constant length of a column of liquid medium between the transducer and the belt.

25. Apparatus according to claim 19 wherein a transducer assembly is mounted to a lever arm for pivotal movement towards or away from the belt, bias means urging the transducer assembly towards the belt, and belt tracking means for maintaining a constant separation between the belt and the transducer assembly.

* * * * *